United States Patent [19]

Adrian

[11] 4,190,363
[45] Feb. 26, 1980

[54] DEVICE FOR MEASURING CONCENTRATION OF A GAS

[76] Inventor: Werner Adrian, Im Roth 19, Ettlingen-Oberweier, Fed. Rep. of Germany, 7505

[21] Appl. No.: 805,334

[22] Filed: Jun. 10, 1977

[30] Foreign Application Priority Data

Jun. 14, 1976 [DE] Fed. Rep. of Germany ....... 2626642

[51] Int. Cl.² .......................................... G01N 21/22
[52] U.S. Cl. ................................... 356/246; 250/343; 356/437; 356/440
[58] Field of Search ............... 356/201, 246, 436, 437, 356/438, 439, 440; 250/343; 23/DIG. 8; 128/2 C

[56] References Cited

U.S. PATENT DOCUMENTS

| | | | |
|---|---|---|---|
| 3,792,272 | 2/1974 | Harte et al. | 356/201 UX |
| 3,997,786 | 12/1976 | Lauer et al. | 356/201 X |

FOREIGN PATENT DOCUMENTS 2310562 12/1976 France ...................................... 356/201

*Primary Examiner*—John K. Corbin
*Assistant Examiner*—Matthew W. Koren
*Attorney, Agent, or Firm*—Colton & Stone, Inc.

[57] ABSTRACT

A device for measuring concentration of a gas adapted to be used for measuring the concentration of alcohol molecules in exhaled breath. The device relies for its operation on the known phenomenon that radiation is absorbed by different materials at different characteristic wavelengths. Radiation of a wavelength which will be absorbed by the gas to be tested is focused into the end of a tube the internal surface of which is highly polished or formed with a layer of material which is totally internally reflecting at the wavelength used and a radiation detector is located at the opposite end of the tube.

Partly to increase the path length by causing many internal reflections to occur and partly to reduce the overall size of the device, the tube is curved either in the form of a helix with constant or varying radius of curvature or is curved first one and then the next in a serpentine fashion.

Gas whose concentration is to be measured is introduced through a side tube which includes a saliva trap if to be used for measuring alcohol molecule concentration in exhaled breath.

The source of radiation comprises an ellipsoidal quartz-halogen lamp of the type which is vacuum-coated with gold.

12 Claims, 2 Drawing Figures

DEVICE FOR MEASURING CONCENTRATION OF A GAS

FIELD OF INVENTION

This invention relates to a device for measuring the concentration of a gas particularly alcohol vapour. In this specification the term "gas" will be used to mean any gaseous or vaporised substance.

BACKGROUND TO THE INVENTION

In the known devices for measuring the concentration of gases by radiation absorption at characteristic absorption wave lengths for the gas, the gas to be analysed is introduced into a measuring chamber. This is subjected to radiation of the specific wave length which enters the measuring chamber with a flux $\phi_o$. This flux is weakened if gas molecules having a significant absorption characteristic at that wavelength are present and if present, the radiation leaves the measuring chamber with a reduced flux $\phi$.

According to Lambert-Beer's law, the relationship is written:

$$\phi = \phi_o e^{-mlc}$$

where
- m is a material constant,
- l is the length of the radiation path in the absorbing medium, and
- c is the concentration of the absorbing gas in the measuring chamber.

If it is desired to measure very small concentrations, then, for a minimum weakening ratio which is given by the relationship $\phi/\phi_o$ and is limited by the resolution and sensitivity of the detectors and amplifiers, this is only possible by increasing the path length l of the radiation through the chamber.

In known spectrophotometric devices for gas analysis, measuring chambers are used in which the radiation path is bent via an optical system. For example, a principle given by White makes it possible to produce path lengths of up to ten meters. However, the apertures are small and the volume of the chamber amounts to more than six liters. For measuring the concentration of alcohol molecules in exhaled breath, the measuring chamber must have a very small volume in order to ensure that only alveolar, breathed air fills the measuring chamber. For this reason the chamber volume must not exceed 100 cm$^3$.

PRIOR ART

A device is described in U.S. Pat. No. 3,319,071 in which a sphere with highly reflective inner walls forms the measuring chamber. However, this arrangement is quite unsuitable for measuring the concentration of alcohol in the breath, as a sphere has the greatest volume with the smallest outer dimensions and exactly the opposite desired.

OBJECT OF THE INVENTION

On this basis, it is the object of the invention to produce a device with a measuring chamber having an extremely small volume, a long radiation path and a large aperture.

THE INVENTION

According to the present invention a measuring chamber for a device for measuring the concentration of a gas comprises a curved tube into which the gas can be introduced, the internal surface of which is highly reflective of radiation at the absorption wavelength of that gas. The internal surface of the tube may be highly polished or may have formed thereon a multiple layer of a material having a suitable refractive index so total internal reflection of radiation at the critical wavelength can be obtained.

Conveniently one end of the tube is flared in the form of a trumpet and comprises a radiation inlet and the other end comprises an outlet for the radiation after it has passed through the tube.

Preferably a window which is conveniently in the form of a converging lens or part of a converging lens assembly is provided at the outlet end of the tube to focus the exiting radiation onto a detector.

By curving the tube and causing internal reflections to occur, so the radiation path length is longer than the actual length of the tube.

The tube may be coiled one or more times to form a helix or curved first one way and then another in serpentine fashion.

Preferably the gas is introduced through a side tube which communicates with an opening in the wall of the first mentioned tube.

Preferably the opening is near the outlet end of the first mentioned tube.

Where the measuring chamber is to be fitted to a device for measuring the concentration of alcohol in exhaled breath, the side tube preferably includes or is connected to a saliva trap between a nozzle at the free end of the tube and the said opening in the wall of the first mentioned tube.

Preferably the source of radiation comprises an ellipsoidal quartzhalogen lamp of the type which is vacuum-coated with gold. The rays are concentrated at the second focal point of the ellipsoid. Due to the length of the coil and irregularities usually present in the surface of the ellipsoidal mirror, a "point" of focus of approximately 6 mm diameter is obtained. For the purpose of the invention this is sufficiently punctiform. This point of focus is formed on the radiation inlet of the measuring chamber. The radiation leaving this enters the tube and after reflection on the optically effective surfaces of the inner wall of the tube it reaches the radiation outlet from where it passes to the detector.

In this way, with a small chamber volume long effective path lengths can be obtained with a good degree of efficiency, as the flux of radiation beamed into the tube is only weakened by a very small amount.

The invention will now be described by way of example with reference to the accompanying drawing.

DESCRIPTION OF EMBODIMENTS OF THE INVENTION

Figure 1:
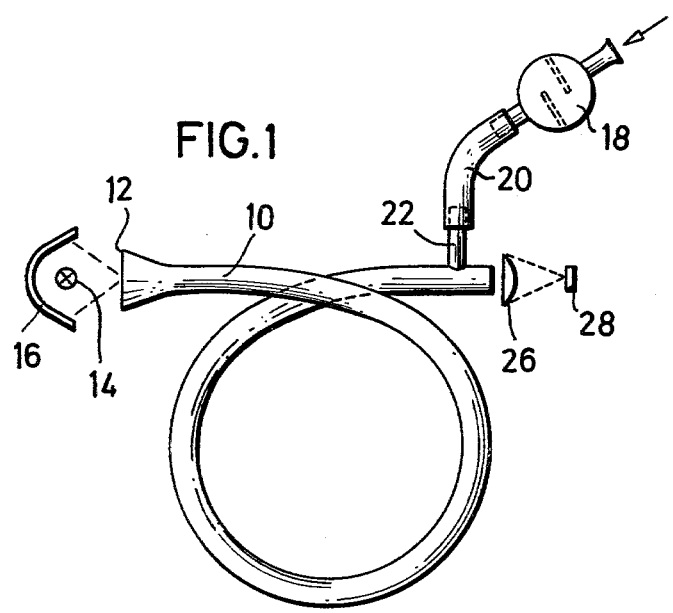
FIG. 1 shows one embodiment in which the measuring chamber comprises a coiled tube.

In FIG. 1 a tube 10 is coiled around to form a single turn helix having a substantially constant radius of curvature. A radiation entrance is provided by flaring one end of the tube 10 to form a trumpet shape 12. This ensures that not only focused but also scattered/diverging radiation will be picked up by the tube entrance.

Radiation is provided by an ellipsoidal quartz-halogen lamp of the type which is vacuum-coated with gold. Such a lamp is shown diagrammatically as comprising a filament 14 and elliptical reflector 16. The trumpet entrance 12 is located so as to receive the focused radiation from the reflector 16.

The interior surface of the tube 10 can be of two types. Either it can be highly polished so as to be highly reflective at the wavelength of the radiation from the lamp 14, 16 or a multiple layer is vacuum deposited thereon of a material having a refractive index n such that total internal reflection of the radiation from the lamp occurs if the radiation impinges thereon at an acute angle.

Gas to be measured is blown into the tube 10 via nozzle 18 and flexible tube 20 which is fitted to a side tube 22 of the main tube 10. A saliva trap 24 is located between the nozzle 18 and the flexible tube 20. Any residual air/gas in the main tube 10 is displaced through the trumpet end 12 by blowing in the gas to be measured through the nozzle 18. A lens 26 closes the other end of the tube 10 (near to the inlet port from the side tube 22) to prevent the loss of gas therethrough.

The lens 26 is transparent at the wavelength of the radiation from the lamp 14, 16 and focuses any radiation arriving at that end of the tube 10 from the lamp onto a detector shown diagrammatically at 28.

Figure 2:
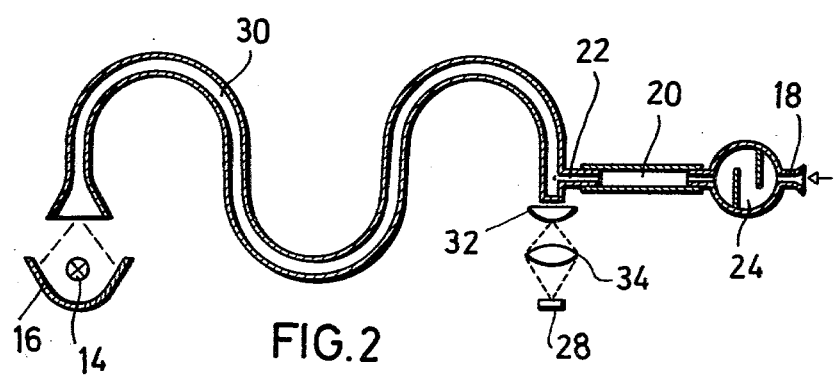
FIG. 2 shows another embodiment in which the tube forming the measuring chamber is serpentine shaped.

In the FIG. 2 embodiment the tube 30 is bent first one way and then the next in serpentine fashion. The radius of curvature at each bend is substantially the same but need not be so and to advantage may be different.

The provisions for introducing radiation and gas into the tube 30 are all as described with reference to FIG. 1. However the converging lens 26 of FIG. 1 has been replaced by a converging lens assembly 32, 34.

When the tube is coiled into a helix having more than one turn the radius of curvature for each of the turns in the helix may be the same or different, thus producing for example a spiral effect.

I claim:

1. In a device for measuring the concentration of a gas of the type in which a sample of the gas to be measured is introduced into a chamber through which radiation is passed from a source to a detector, and in which the radiation is selectively absorbed by the gas, the improvement wherein:

the chamber is formed from a curved tube, through which the radiation can pass from one end to the other, the interior surface of the tube being highly reflective of radiation at the absorption wavelength of the gas, the tube having an inlet adjacent one of its ends for introducing the gas to be measured and an outlet at the opposite end thereof for discharging the gas, the wall of the tube between the inlet and the outlet being imperforate.

2. A device as set forth in claim 1 in which the internal surface of the tube is highly polished.

3. A device as set forth in claim 1 in which on the internal surface of the tube there is formed a multiple layer of a material having a refractive index such that radiation at the absorption wavelength is totally internally reflected thereby.

4. A device as set forth in claim 1 in which one end of the tube is flared in the form of a trumpet and serves as an inlet for radiation and the other end includes a window through which radiation can pass to the detector.

5. A device as set forth in claim 4 in which the window comprises a converging lens.

6. A device as set forth in claim 1 further comprising a side tube through which the gas to be measured is introduced, and the tube includes an opening in the wall thereof, which communicates with the said side tube.

7. A device as set forth in claim 6 further comprising a nozzle into which exhaled breath can be blown and a saliva trap between the nozzle and the said side tube.

8. A device as set forth in claim 6 in which the said opening in the tube wall is near the end of the tube from which the radiation leaves.

9. A device as set forth in claim 1 in which the tube is coiled to form a helix.

10. A device as set forth in claim 9 in which the radius of curvature of some of the turns in the helix is different from that of other turns in the helix.

11. A device as set forth in claim 1 in which the tube is curved first one way and then the other in a serpentine fashion.

12. A device as set forth in claim 1 in which the source of radiation comprises an ellipsoidal quartz-halogen lamp of the type which is vacuum-coated with gold.

* * * * *

UNITED STATES PATENT OFFICE
CERTIFICATE OF CORRECTION

PATENT NO. : 4,190,363
DATED : February 26, 1980
INVENTOR(S) : Werner Adrian

It is certified that error appears in the above—identified patent and that said Letters Patent are hereby corrected as shown below:

The formula at Col. 1, line 25 should read:

$$\phi = \phi_0 e^{-mlc}$$

Signed and Sealed this

Seventeenth Day of June 1980

[SEAL]

Attest:

SIDNEY A. DIAMOND

Attesting Officer     Commissioner of Patents and Trademarks